United States Patent

Cavazza

(10) Patent No.: US 6,515,020 B1
(45) Date of Patent: Feb. 4, 2003

(54) COMBINATION OF CARNITINES AND RESVERATROL FOR PREVENTION OR TREATMENT OF CEREBRAL AND AGEING DISORDERS

(75) Inventor: Claudio Cavazza, Rome (IT)

(73) Assignee: Sigma-Tau HealthScience S.p.A., Pomezia (IT)

( * ) Notice: Subject to any disclaimer, the term of this patent is extended or adjusted under 35 U.S.C. 154(b) by 0 days.

(21) Appl. No.: 09/806,454

(22) PCT Filed: Oct. 6, 1999

(86) PCT No.: PCT/IT99/00311

§ 371 (c)(1),
(2), (4) Date: Mar. 30, 2001

(87) PCT Pub. No.: WO00/21526

PCT Pub. Date: Apr. 20, 2000

(30) Foreign Application Priority Data

Oct. 9, 1998 (IT) ............................ RM980636

(51) Int. Cl.⁷ .................... A61K 31/225; A61K 31/205; A61K 31/70; C07C 69/34; C07C 229/00
(52) U.S. Cl. ......................... 514/547; 514/25; 514/470; 514/556; 514/733; 514/822; 560/196; 562/567
(58) Field of Search .................. 562/567; 514/822, 514/733, 470, 25, 547, 556; 560/196

(56) References Cited

U.S. PATENT DOCUMENTS 4,346,107 A * 8/1982 Cavazza et al.
5,747,536 A * 5/1998 Cavazza
5,904,924 A   5/1999 Gaynor et al.

FOREIGN PATENT DOCUMENTS

| EP | 0 773 020 | 5/1997 |
| WO | WO98/33494 | 8/1998 |
| WO | WO98/41113 | 9/1998 |
| WO | WO99/01148 | 1/1999 |
| WO | WO 99/01148 A1 * | 1/1999 |
| WO | WO99/59561 | 11/1999 |

OTHER PUBLICATIONS

Wang Z–Z et al.: "Reducing effect of 3,4'5–trihydroxystibene–3–beta–mono–d–glucoside on arterial thrombosis induced by vascular endothelial injury" Zhongua Yaoli Xuebao–Acta Pharmacologica sinica, CN, Shanghai, vol. 16, No. 2, Mar. 1995, pp. 159–162.

Heuberger W et al.: "Increased urinary excretion of carnitine in patients treated with cisplatin." European Journal of Clinical Pharmacology, Sep. 1998, 54 (7) 503–8.

Elattar T M et al.: "Modulating effect of resveratrol and quercetin on oral cancer cell growth and proliferation." Anti–Cancer Drugs, Feb. 1999, 10 (2) 187–93.

* cited by examiner

Primary Examiner—Johann Richter
Assistant Examiner—Paul A. Zucker
(74) Attorney, Agent, or Firm—Nixon & Vanderhye P.C.

(57) ABSTRACT

A pharmaceutical product which comprises admixed or separately packaged (A) L-Carnitine or an alkanoyl L-canitine and (B) a trihydroxy- or tetrahydroxystilbene such as resveratrol is useful for the prevention and treatment of pathological neuronal or cerebral disorders.

8 Claims, No Drawings

COMBINATION OF CARNITINES AND RESVERATROL FOR PREVENTION OR TREATMENT OF CEREBRAL AND AGEING DISORDERS

This is a 35 U.S.C. § 371 of PCT/IT99/00311 filed Oct. 6, 1999.

The present invention relates to a new use of a combination composition of L-carnitine or an alkanoyl L-carnitine and a trihydroxy or tetrahydroxystilbene for the preventive or therapeutic treatment of cerebral disorders brought about by ageing and use of neurotoxic drugs.

Accordingly, the composition may take the form and exert the action of a dietary supplement or of an actual medicine, depending upon the support or preventive action, or the strictly therapeutic action, which the composition is intended to exert in relation to the particular individuals it is to be used in.

The use of the combination of (A) L-carnitine or alkanoyl L-carnitine in which the straight or branched-chain alkanoyl group contains 2–8 carbon atoms, or a pharmacologically acceptable salt thereof and (B) a trihydroxy or tetrahydroxystilbene, typically resveratrol, in the prevention and therapeutic treatment of a number of different pathologies is already known. U.S. Pat. No. 5,747,536, in fact, describes the use of the aforesaid combination for the prevention and treatment of diabetic neuropathy and atheroslerotic lesions and for the inhibition of platelet aggregation.

The use according to the present invention is in no way related to or deducible from such already known use.

In its broader aspect, the present invention relates to the coordinated use of L-carnitine or alkanoyl L-carnitine or their pharmacologically acceptable salts and of a trihydroxy or tetrahydroxystilbene for the prevention or treatment of the above-mentioned pathologies, where what is meant by the "coordinated use" of these active ingredients is indifferently either their co-administration, i.e. the practically simultaneous administration of L-carnitine or alkanoyl L-carnitine or their pharmacologically acceptable salts and trihydroxy- or tetrahydroxystilbene, or the administration of a composition containing a mixture of said active ingredients.

Here below, for the sake of brevity and simplicity of presentation, reference will be made only to L-carnitine, it being understood that the description also applies to the above-mentioned alkanoyl L-carnitines and their pharmacologically acceptable salts. Equally, here below, reference will be made only to resveratrol (trans-3,4',5-trihydroxystilbene), it being understood, however, that the description applies not only to cis-resveratrol and to the respective trans- and cis-glycosides, but also to the trihydroxy- and tetrahydroxystilbenes in general.

Resveratrol is to be found in grapes and in particular in grape skins, seeds, stalks and vine leaves, particularly of *Vitis vinifera, Vitis rotundifolia* and *Vitis labrusca* and, obviously, in the wines obtained from their grapes and in the extracts and powders of the above-mentioned natural products. Resveratrol is also present in the roots of a number of species of the *Polygonum* genus (*Polygonaceae* family), such as *Polygonum cuspidatum* and *Polygonum multiflorum*.

For the purposes of the present invention, what is meant by "resveratrol" is both trans-3,4'-5-trihydroxystilbene (i.e. resveratrol proper) and the cis isomer, the respective glycosides and extracts and powders containing resveratrol obtained from any suitable plant species.

The natural polyphenols present in grapes and wine have recently claimed the attention of numerous groups of researchers following epidemiological studies which have demonstrated that populations which consume moderate amounts of wine in their habitual diet present a much lower percentage of cardiovascular accidents than do populations whose dietary habits do not include the consumption of wine. Among the various polyphenols studied, resveratrol has proved to be the most interesting in that it is capable of exerting a significant action against platelet aggregation as well as a significant anti-inflammatory and vasoprotective action.

Another aspect of resveratrol and the polyphenols present in wine is that related to the significant reduction in the incidence of pre-senile and senile dementia which moderate consumption of wine is capable of inducing, particularly in the elderly population. A recent epidemiological study conducted in a large population has confirmed what a similar previous study had already indicated with regard to the mortality due to cerebral stroke, which is lower in moderate wine drinkers than in non-drinking subjects.

As regards the already known therapeutic uses of L-carnitine, this substance is used for example in the cardiovascular field for the treatment of acute and chronic myocardial ischaemia, angina pectoris, heart failure and cardiac arrhythmias and for peripheral vasculo-pathies. In the nephrological field, L-carnitine is administered to chronic uraemic patients undergoing regular haemodialytic treatment to combat muscular asthenia and the onset of muscle cramps. Other therapeutic uses relate to the normalisation of the HDL/LDL+VLDL ratio and total parenteral nutrition. The use of L-carnitine is also known in the treatment of certain myopathies and muscular dystrophies.

It has now been found surprisingly that a composition containing a combination of the following as its characterising components:

(A) L-carnitine or an alkanoyl L-carnitine wherein the alkanoyl is a straight or branched-chain alkanoyl group containing 2–8 carbon atoms, or a pharmacologically acceptable salt thereof; and (B) a trihydroxy or tetrahydroxystilbene is extremely effective in the prevention and/or therapeutic treatment of cerebral disorders caused by ageing or by the use of neurotoxic drugs, as a result of the potent synergistic effect exerted by its components.

Therefore, the present invention relates to the use of (A) L-carnitine or an alkanoyl L-carnitine wherein the alkanoyl is a straight or branched-chain group containinig 2–8 carbon atoms, or a pharmacologically acceptable salt thereof, and (B) a trihydroxy or tetrahydroxystilbene to prepare a pharmaceutical product in which (A) and (B) are admixed together or separately packaged for the prevention and treatment of disease forms related to neuronal or cerebral disorders. That the active ingredients (A) and (B) can be admixed together or separately packaged is consistent with what has been said above with regard to the "co-ordinated use" of said ingredients.

Preferably, the alkanoyl group contains 2–6 carbon atoms and, even more preferably, is selected from the group consisting of acetyl, propionyl, butyryl, valeryl and isovaleryl L-carnitine.

Component (B) is preferably 3,4',5-trihydroxystilbene (resveratrol) or 3,4',5-trihydroxy-3-β-mono-D-glucoside or one of their pharmacologically acceptable salts. The resveratrol can be the synthetically prepared form or can be the form extracted from *Vitis vinifera, Vitis rotundifolia, Vitis labrusca* or from the roots of *Polygonum cuspidatum* or *Polygonum multiflorum*.

Component (B) can also consist in extracts or powders of natural products containing resveratrol, such as extracts or powders of grape skins, seeds or stalks of *Vitis vinifera, Vitis rotundifolia, Vitis labrusca* or from the roots of *Polygonum cuspidatum* or *Polygonum multiflorum*.

The (B):(A) weight-to-weight ratio ranges from 1:1 to 1;1,000, and preferably from 1:1 to 1:500.

The cerebral disorders caused by ageing prophylactically and therapeutically treated according to the present invention include particularly cerebral stroke, pre-senile and senile dementia and Alzheimer's disease.

An example of a neurotoxic drug against the effects of which the "co-ordinated" use according to the invention proves potently effective is cisplatin.

The unexpected synergism exerted by components (A) and (B) at cerebral nerve level is demonstrated by the results obtained with experimental models well recognised as being indicative of a protective action at central nervous system level and as being predictive of the effective use of the combination to combat cerebral nerve abnormalities in human subjects.

Toxicology

Tests conducted both in mice and in rats, administering combinations of high doses both of L-carnitine and its alkanoyl derivatives and of resveratrol or grape extracts containing polyphenols with a resveratrol content of approximately 0.1% have demonstrated the low toxicity and good tolerability of the composition according to the invention. The oral administration, in rats, of up to 1 g/kg of L-carnitine or its alkanoyl derivatives together with high doses of resveratrol (up to and above 0.5 mg/kg) or with grape extracts (up to and above 1 g/kg) revealed no toxic reactions worthy of note. Similarly well tolerated appeared to be the prolonged administration with the diet every day for three consecutive months of combinations either of L-carnitine or its alkanoyl derivatives plus resveratrol or grape extracts containing resveratrol at doses equal to a quarter of the doses used in the previously mentioned forms. At the end of this treatment, no abnormalities of the various biological parameters considered (weight gain, haematocrit, serum glucose, BUN, etc.) or of the histological findings in the main organs examined (liver, heart, lungs, kidneys, adrenal glands, gonads) were detected. We also report here below a number of tests whose findings provide evidence of the substantial synergism exerted by the new composition containing carnitine or its alkanoyl derivatives and resveratrol or its derivatives at the cerebral nervous system level. Tests on the effect of carnitines and resveratrol alone or in combination on behavioural reaction abnormalities One of the effects of a vasoactive peptide and neuromodulator such as endothelin is the influence it exerts on animal behaviour in reducing the animals' motility and vestibular reactions.

In these tests, we were able to observe that the typical action of endothelin (ET-1) injected intracerebrally in mice at the dose of 1 pmol/mouse, which is to substantially reduce the animals' spontaneous motility, can be inhibited to a very significant extent by prior administration of carnitines and resveratrol, and, particularly, that the combination of these two types of substances is capable of acting synergistically, restoring the motility reduced by endothelin administration almost to normal values.

The values were observed, keeping 10 mice at a time placed in a container with a photocell and an automatic movement counter; the count was done by observing the mice for periods of 5 minutes 15 minutes after the endothelin (ET-1) injection.

The motility reduction percentages observed were 85.5% for endothelin alone and 69.6–65.5% and 60.3% for L-carnitine, acetyl L-carnitine and propionyl L-carnitine, respectively, which were administered intra-peritoneally to the animals at the dose of 300 mg/kg for the three days preceding the experiment and half an hour before the ET-1 injection.

Resveratrol alone (2.5 mg/kg) led to a 60.4% reduction and approximately the same reduction was achieved with a grape extract containing polyphenols and titred in resveratrol. However, the combination of resveratrol and carnitine restored the motility of the endothelin-treated animals almost to normal values. In the case of the combined administration of resveratrol and propionyl L-carnitine, the number of movements of the animals was practically identical to that of control animals, thus demonstrating an unexpected synergistic potentiation of the effects.

Significant synergistic activity was also detectable with the use of resveratrol or natural polyphenolic products containing resveratrol in combination with acetyl L-carnitine or, though to a lesser extent, with L-carnitine. Tests of survival of pheochromocytoma cells (PC-12) exposed to $H_2O_2$ and treated with L-carnitine or resveratrol or with the two products in combination A culture of pheochromocytoma cells (PC-12) containing $3 \times 10^5$ N-cells/ml was exposed to 0.1 mM concentrations of $H_2O_2$ for 30 minutes. While the survival of the cells treated with $H_2O_2$ alone was approximately 45% after 24 hours, the survival of the cells treated with L-carnitine or with resveratrol was substantially greater, with survival rates of 55, 60 and 62%, respectively, for cells treated with L-carnitine, acetyl L-carnitine and propionyl L-carnitine at concentrations of $10^{-8}$ M, and a survival rate of 69% for cells treated with resveratrol at the concentration of $10^{-4}$ M.

The survival rate was 88% with the combination of acetyl L-carnitine and resveratrol at the concentrations used previously, thus demonstrating a synergistic effect of the substances considered.

Moreover, with this combination, unlike the other cases, no signs of cell degeneration were detectable.

Tests on the protective effect of carnitines, resveratrol and combinations of these on sensory neuronal lesions induced by cisplatin In these tests, cisplatin was used as a neuronal toxic factor, capable, particularly, of producing lesions in the sensory neurones and thus of impairing proprioceptive perception. The tests evaluated the ability of carnitines, resveratrol and combinations of these substances to restore peripheral sensory perception in the mouse impaired by injection of cisplatin. This ability was assessed by evaluating the reaction to thermal pain induced by a heated water solution in which the animals' tails were dipped according to the tail-flick test, or using the rotating bar test (Apfel S.C., Lipton R.B., *Ann. Neurol.*, 29, 87–90, 1991).

Cisplatin was administered subcutaneously at the dose of 10 mg/kg for eight consecutive days. Over the same period the mice received injections of 100 mg/kg of carnitines and 2.5 mg/kg of resveratrol or combinations of these products.

The results of these two tests provide evidence of a potent protective action afforded by the combination, which is particularly marked in the case of the combinations of acetyl L-carnitine and propionyl L-carnitine with resveratrol or with a grape extract containing resveratrol.

In these cases, the response to the pain stimulus was restored to normal levels (the response to pain was increased by approximately 2° C. as compared to controls in the animals treated with the combination).

Also in the rotating bar test, whereas the duration of the equilibrium time in the control animals (10 animals per group) was 14.6 seconds (reduced to approximately 8 seconds in the cisplatin-treated animals), a significant increase in equilibrium time was noted both in the group treated with carnitines and in the group treated with resveratrol. The increase proved highly significant, however, in the group of 5 animals treated with the test combination. The values observed, in fact, were 13.5 seconds in the animals treated with acetyl L-carnitine plus resveratrol and 14.4 seconds in those treated with propionyl L-carnitine plus resveratrol.

These tests, too, demonstrate an unexpected synergism between carnitines and resveratrol.

Illustrative, non-limiting examples of formulations according to the invention are reported hereinbelow.

| | | |
|---|---|---|
| 1) L-carnitine | mg | 500 |
| resveratrol | mg | 5 |
| 2) Acetyl L-carnitine | mg | 500 |
| resveratrol | mg | 5 |
| 3) Propionyl L-carnitine | mg | 500 |
| resveratrol | mg | 5 |
| 4) Isovaleryl L-carnitine | mg | 500 |
| resveratrol | mg | 5 |
| 5) L-carnitine | mg | 500 |
| lyophilized dry grape exctract | mg | 250 |
| (titled mg 0,5% of resveratrol) | | |
| 6) Acetyl L-carnitine | mg | 500 |
| lyophilized dry grape exctract | mg | 250 |
| (titled mg 0,5% of resveratrol) | | |
| 7) Propionyl L-carnitine | mg | 500 |
| lyophilized dry grape exctract | mg | 250 |
| (titled mg 0,5% of resveratrol) | | |
| 8) Isovaleryl L-carnitine | mg | 500 |
| lyophilized dry grape exctract | mg | 250 |
| (tilted mg 0,5% of resveratrol) | | |
| 9) L-carnitine | mg | 500 |
| resveratrol | mg | 5 |
| tocopherol acetate | mg | 20 |
| β-carotene | mg | 10 |
| 10) L-carnitine | mg | 500 |
| lyophilized grape exctract | mg | 250 |
| (titled mg 0,5% of resveratrol) | | |
| tocopherol acetate | mg | 20 |
| β-carotene | mg | 10 |
| 11) L-carnitine | mg | 500 |
| resveratrol | mg | 5 |
| tocopherol acetate | mg | 20 |
| Vit. C | mg | 100 |
| Selenium | mg | 40 |
| 12) Acetyl L-carnitine | mg | 250 |
| resveratrol | mg | 2.5 |
| phosphatidylcholine | mg | 50 |
| phosphatidylserine | mg | 50 |
| glycerylphosphorylcoline | mg | 50 |
| 13) Acetyl L-carnitine | mg | 250 |
| grape's polyphenols | mg | 100 |
| resveratrol | mg | 2,5 |
| phosphatidylcholine | mg | 50 |
| phosphatidylserine | mg | 50 |
| glycerylphosphorylcoline | mg | 50 |
| Vit. E | mg | 10 |
| selenium | mg | 10 |
| magnesium | mg | 5 |
| zinc | mg | 3 |
| 14) Acetyl L-carnitine | mg | 250 |
| grape's polyphenols | mg | 100 |
| resveratrol | mg | 2.5 |
| Vit. B1 | mg | 1 |
| Vit. B2 | mg | 1 |
| Vit. B6 | mg | 2 |
| pantethine | mg | 5 |
| serine | mg | 10 |
| choline | mg | 10 |
| arginine | mg | 10 |
| lysine | mg | 10 |

What is meant by pharmacologically acceptable salt of L-carnitine or alkanoyl L-carnitine is any salt of these active ingredients with an acid that does not give rise to unwanted toxic or side effects. These acids are well known to pharmacy experts.

Non-limiting examples of suitable salts are the following: chloride; bromide; iodide; aspartate, acid aspartate; citrate, acid citrate; tartrate; phosphate, acid phosphate; fumarate, acid fumarate; glycerophosphate; glucose phosphate; lactate; maleate, acid maleate; orotate; oxalate, acid oxalate; sulphate, acid sulphate; trichloroacetate; trifluoroacetate; and methanesulphonate.

A list of FDA-approved pharmacologically acceptable salts is given in *Int. J. of Pharm.* 33, (1986), 201–217; this latter publication is incorporated herein by reference.

The aforesaid compositions associations can be prepared to be administered orally, parenterally, rectally or transdermally in solid, semi-solid, liquid, semi-liquid, pulverulent, granular or liposomic form.

In additon to the characterizing ingredients (a) and (b) the combination composition may also comprise one or more of the following components: polyphenols, anthocyanins, tannins, antho-cyanosides, vitamins, coenzymes, minerals salts, vegetable fibres, phosphatidylcholine, phosphatidylserine, glycerylphosphorylcoline, ginseng and Ginko biloba exctracts, vitamins and antioxidants.

What is claimed is:

1. A therapeutic method of treating cerebral stroke, loss of memory, pre-senile dementia, Alzheimer's disease or preventing or treating disorders elicited by the use of neurotoxic drugs, which method comprises administering to a patient in need thereof an effective amount of admixed or separately packaged:

(A) L-carnitine or an alkanoyl L-carnitine wherein the alkanoyl is a straight or branched-chain group containing 2–8 carbon atoms or a pharmacologically acceptable salt thereof; and (B) a trihydroxy or tetrahydroxystilbene.

2. The method of claim 1, wherein the alkanoyl contains 2–6 carbon atoms.

3. The method of claim 2, wherein the alkanoyl is selected from the group consisting of acetyl, propionyl, butyryl, valeryl and isovaleryl.

4. The method of claim 1, wherein component (B) is 3,4',5-trihydroxystilbene (resveratrol) or 3,4',5-trihydroxystilbene-3-β-mono-D-glucoside or a pharmacologically acceptable salt or ester thereof.

5. The method of claim 4, wherein resveratrol is resveratrol extracted from *Vitis vinifera, Vitis rotundifolia* or *Vitis labrusca*.

6. The method of claim 1, wherein component (B) consists of extracts or natural product powders of grape skin or of grape stalks of *Vitis vinifera, Vitis rotundifolia* or *Vitis labrusca* and of *Polygonum cuspidatum* or *Polygonum multiflorum roots*.

7. The method of claim 1, wherein the weight ratio (B):(A) is from 1:1 to 1:1,000.

8. The method of claim 1, wherein the weight ratio (B):(A) is from 1:1 to 1:500.

* * * * *